United States Patent [19]
Chang

[11] Patent Number: 5,469,069
[45] Date of Patent: Nov. 21, 1995

[54] METHOD AND APPARATUS FOR MEASURING RESISTIVITY OF GEOMETRICALLY UNDEFINED MATERIALS

[76] Inventor: On-Kok Chang, 1031 Belvedere La., San Jose, Calif. 95129

[21] Appl. No.: 35,142

[22] Filed: Mar. 19, 1993

[51] Int. Cl.⁶ ............................................. G01R 27/02
[52] U.S. Cl. ................................... 324/693; 324/722
[58] Field of Search .............................. 324/693, 722, 324/724, 450

[56] References Cited

U.S. PATENT DOCUMENTS

| | | | |
|---|---|---|---|
| 3,434,045 | 3/1969 | Rogstad et al. | 324/450 |
| 4,137,495 | 1/1979 | Brown | 324/450 |
| 4,342,964 | 8/1982 | Diamond et al. | 324/450 |

FOREIGN PATENT DOCUMENTS

| | | | |
|---|---|---|---|
| 0030055 | 2/1984 | Japan | 324/450 |
| 0167461 | 7/1987 | Japan | 324/450 |

OTHER PUBLICATIONS

Research Disclosure May 1977.
Cell for Simultaneous Measurement of Electric Conductivity and Thermo–EMF of Dissociated Compounds Ditman et al. Aug. 1977.

*Primary Examiner*—Maura K. Regan

[57] ABSTRACT

The present invention is directed to an apparatus and method for improving the accuracy of measuring resistivity and/or conductivity of a paste. Exemplary embodiments relate to an apparatus for measuring electrical characteristics of a material. A sample of material is placed in a first charge conducting region with a first cross-sectional area and in a second charge conducting region with a second cross-sectional area, the first cross-sectional area being greater than the second cross-sectional area. Further, the apparatus conducts an electric charge through the first and second charge conducting regions via a conductive terminal located in the first charge conducting region.

13 Claims, 1 Drawing Sheet

5,469,069

METHOD AND APPARATUS FOR MEASURING RESISTIVITY OF GEOMETRICALLY UNDEFINED MATERIALS

BACKGROUND OF THE INVENTION

1. Field of the Invention

The present invention relates generally to measuring the electrical characteristics of a material, and more particularly to measuring the resistivity or conductivity of materials which do not possess a defined geometry, such as conductive pastes.

2. State of the Art

Techniques for measuring the conductivity of a material are well known. Conductivity corresponds to the inverse of resistivity, and these two electrical characteristics can easily be correlated to one another.

Typically, the conductivity of a material is measured by contacting two probes (e.g., the probes of a conventional ohmmeter) to opposite ends of the material. A constant electrical current is passed via the two probes through the material. By measuring this current for a given voltage across the two probes, the resistance, and thus the conductivity, of the material can be determined.

The foregoing measurement technique is relatively accurate for detecting conductivity of solid materials having a relatively well defined geometry. However, such a measurement is relatively inaccurate for measuring the conductivity of materials which do not have well defined geometries, such as pastes and other similar materials. Because processes involving paste are common in industries such as the battery industry, conductivity measurements represent an important property of the paste.

Another conventional technique for measuring the conductivity of materials, such as paste, is to use two metal plates for forming a slab of paste therebetween. Conductivity or resistivity can then be measured between the two metal plates. However, this method is also inaccurate because contact between the metal plates and the material is not reproducible.

The inaccuracy of conductivity tests for materials which do not possess well defined geometries is due in part to an inability to establish reproducible contact between the probes and the material. Accordingly, there is a need for an apparatus and method which can accurately detect electrical characteristics of materials which do not possess well defined geometries.

SUMMARY OF THE INVENTION

The present invention is directed to an apparatus and method for improving the accuracy of measuring resistivity and/or conductivity of materials such as pastes. As referenced herein, the term "conductivity" is considered to encompass any measurement which can be correlated to a material's ability to conduct an electric charge, including resistivity measurements.

Exemplary embodiments comprise means for receiving a sample of material. The receiving means has a first charge conducting region with a first cross-sectional area and a second charge conducting region with a second cross-sectional area, the first cross-sectional area being greater than the second cross-sectional area. Further, the apparatus includes means for conducting an electric charge through said first and second charge conducting regions, said electric charge conducting means having a conductive terminal for contacting said first charge conducting region.

BRIEF DESCRIPTION OF THE DRAWINGS

Other objects and advantages of the present invention will become more apparent from the following detailed description of the invention when read in conjunction with the accompanying drawings wherein like elements have been similarly labelled and wherein.

DETAILED DESCRIPTION OF THE PREFERRED EMBODIMENTS

Figure 1:
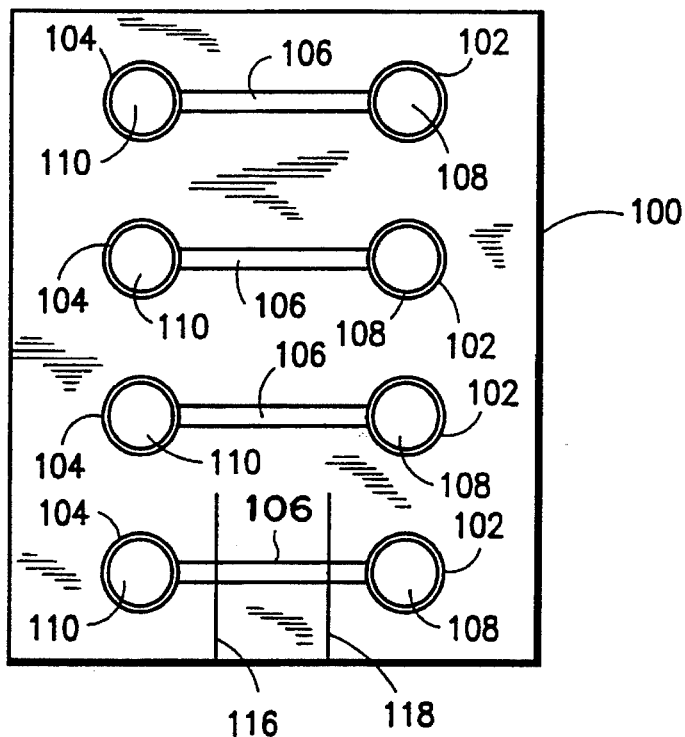
FIG. 1 is a top view of an exemplary embodiment of an apparatus of the present invention.

FIG. 1 illustrates an apparatus for measuring the electrical characteristics of a material. The FIG. 1 apparatus includes a means for receiving a sample of material, generally designated as a block 100. The receiving means has a first charge conducting region with a first cross-sectional area. In the FIG. 1 embodiment, this first charge conducting region is generally designated as including cylindrical well regions 102 and 104.

As referenced herein, the phrase "cross-sectional area" refers to an area of a cross-section of a conductive path through the first charge conducting region. Because the well regions 102 and 104 are of relatively constant diameter along their cylindrical axis, a cross-sectional area of the first charge conducting region corresponds to a surface area of the well region 102 or the well region 104. Thus, the first cross-sectional area can be determined as $\pi r^2$, wherein r is a radius of the well region 102 or 104.

The receiving means further includes a second charge conducting region with a second cross-sectional area. The second charge conducting region is represented in the FIG. 1 apparatus as channel 106. Because conductive charge will flow across the length of the channel 106 from one of the well regions 102 or 104 to the other of the well regions 104 or 102, respectively, the second cross-sectional area corresponds to a width of the channel 106 multiplied by a depth of the channel 106. The channel 106 is formed with a reduced cross-sectional area relative to the cross-sectional area of the cylindrical well regions 102 and 104.

The FIG. 1 apparatus further includes means for conducting an electric charge through the first and second charge conducting regions. For example, in the exemplary FIG. 1 embodiment, metal cylinders 108 and 110 are tightly fit into the cylindrical well regions 102 and 104 formed in the block 100.

Figure 3:
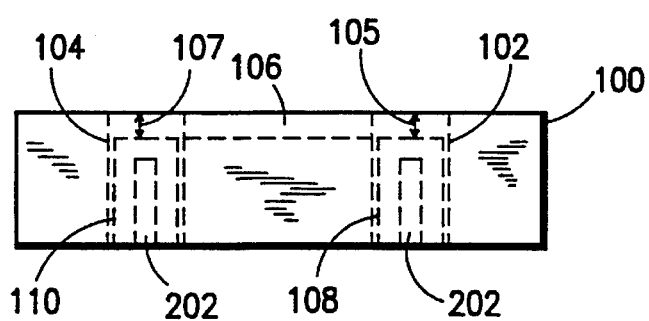
FIG. 3 is a side view from either end of the FIG. 1 embodiment.

As best illustrated in FIG. 3, the axial length of the metal cylinders 108 and 110 is less than the thickness of the block 100 so that recessed portions 105 and 107 are formed at the top of each cylindrical well region. The channel region 106 connects the recessed portions 105 and 107 formed on the top side of the block. Thus, the upper surface of each metal cylinder which is exposed in a recessed portion constitutes a conductive terminal having a cross-sectional area that corresponds to a cross-sectional area of the recessed portion.

Referring still to FIG. 3, each of the metal cylinders is formed with a hole 202 that does not extend the entire way through the metal cylinder. As illustrated in the bottom view of FIG. 2, these holes are exposed on one end (i.e., the bottom) of each metal cylinder, while the opposite end of the metal cylinder is a virtually flat, solid surface.

As illustrated in FIG. 3, it can be seen that the holes 202 are approximately flush with a bottom surface of the metal cylinder, while the top of each metal cylinder is the virtually flat, solid surface used to form a bottom of the recessed portions in each of the cylindrical well regions. The holes 202 in each of the metal cylinders are formed to receive a contact (e.g., probe) for connection to a meter device, such as an ohmmeter.

The flat, solid surface of each metal cylinder is used as a contact area between the conducting means and a material placed within the recessed portion. This contact area generally corresponds to the first cross-sectional area, and is therefore larger in surface area than the second cross-sectional area of the channel 106. Because a cylindrical well region is described with respect to this exemplary embodiment, the contact area between the flat surface of the metal cylinder and paste placed into a recessed portion will be circular.

In an exemplary embodiment, the metal cylinders can be formed of copper. Those skilled in the art will recognize however that a variety of conductive metals can be used.

Further, an exemplary non-conductive material used to form the receiving means can be plastic. This plastic is formed as a rectangular block, with a length of the block being approximately 3¾" long by approximately 3" wide. Each of the cylindrical well regions used to form the first charge conducting region of the receiving means is formed as a cylinder having a circular cross-section with a diameter of approximately ½". The recessed portions 105 and 107 of the cylindrical well regions which are exposed to an interior of the cylindrical well region are approximately ⅛" deep. The channel 106 is formed with a generally square cross-section that is approximately 1/16" deep by approximately 1/16" wide. Thus, a channel region cross-sectional area of an exemplary embodiment corresponds to 1/16"×1/16", representing 2.52 mm². A length of the channel is approximately 25.4 mm.

Those skilled in the art will recognize that the present invention is not limited to first and second regions having any specific shapes or dimensions. Rather, it is only the relative cross-sectional area of the contact area in each well region with respect to the cross-sectional area of the channel region that is significant. While the exemplary shapes and dimensions described above are considered suitable for an exemplary embodiment, it is only necessary to design a contact area having a shape (circular or otherwise) which is larger in cross-sectional area than a cross-sectional area of a charge conducting channel region having any desired shape (square or otherwise).

Further, it should be apparent to those skilled in the art that while only two cylindrical well regions and a single channel connecting the two cylindrical well regions can be used to perform a conductivity test, a plurality of first and second charge conducting regions can be formed in a block to conduct any number of such tests. Four channels and eight cylindrical well regions are illustrated in the FIG. 1 embodiment for the purpose of performing four such tests. Those skilled in the art will appreciate that any number of such regions can be formed in a block of any practical size.

Figure 2:
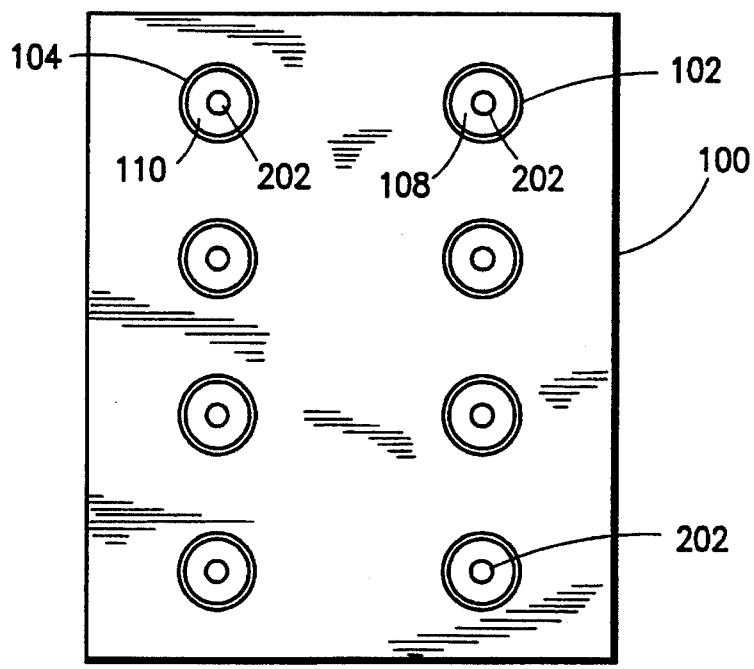
FIG. 2 is a bottom view of the FIG. 1 embodiment.

In operation, a conductivity test can be performed using the apparatus of FIGS. 1–3 as follows. A sample paste can be worked into the two recessed portions in cylindrical well regions 102 and 104. The sample is further worked into the channel 106 connecting the recessed portions. Meter probes from a meter device are inserted into the holes of the metal cylinders for measuring conductivity of paste located between the metal cylinders.

Recessed portions of cylindrical well regions 102 and 104 in conjunction with the channel region 106 for interconnecting the two well regions constitute a measurement area wherein electrical characteristics of a material can accurately be detected in a reproducible manner. Once the paste has been formed into the recessed portions and the channel region of a measuring apparatus, excess paste is removed and conductivity is measured between the metal cylinders. The relatively large contact area between the paste and the virtually flat, solid surface of the metal cylinders in the recessed portions of cylindrical well regions 102 and 104 enhances accuracy of the measurement. This is because the contact area between the paste and the metal is much greater than the cross-sectional area of the channel 106.

Thus, a method for measuring electrical characteristics of a material includes the steps of placing a first portion of a sample of a material into recessed portions of the cylindrical well regions. A second portion of sample material is placed into the charge conducting channel region which interconnects the two recessed portions of cylindrical well regions. An electric charge is then conducted through the first and second portions of the sample from a first of the recessed portions to a second of the recessed portions via the channel region.

As discussed above, the present invention can be used to measure the conductivity and/or resistivity of material such as a conductive paste (e.g., cathode paste). Because the paste is placed into contact with the block 100, exemplary embodiments of the invention include a block formed of Teflon™ or formed with a Teflon™ coating. A material such as Teflon™ is more resistant to organic solvents as a constituent in the paste, or organic solvents used to clean the block between measurements, relative to other polymers.

Those skilled in the art will recognize that the present invention can be applied not only to pastes but to liquids which can be retained in the recessed portions and channel regions. Further, the invention can be applicable to cathode pastes including, for example, vanadium oxide, carbon and similar materials.

While the insertion of probes into the holes of the metal cylinders from the bottom side of the FIG. 3 block can be used to perform a two probe measurement of resistivity, a four probe resistance measurement can also be performed. For example, in an alternate embodiment, two additional contact areas can be formed of thin metal sheets in the block 100. These metal sheets are illustrated in FIG. 1 as metal sheets 116 and 118 which are separated a fixed distance away from one another.

The metal sheets represent voltage probes, which can be used to minimize the effect of any probe-to-sample contact and thus improve overall measurement accuracy. Because the metal sheets are used to perform a voltage measurement, the exposed ends of these sheets which contact the material in the channel 106 can be made very small so that the distance between them can be measured accurately. The small contact area between each of the metal sheets and the material in the channel 106 does not detrimentally affect the accuracy of the voltage measurement because the current that flows through the contact area is very small (e.g., in the microamp or nonoamp range).

The voltage measured across the metal sheets 116 and 118 and the current measured at 108 or 110 can be used to calculate the resistance of the sample located between the metal sheets between 116 and 118. The resistance value calculated by this method is not affected by the contact resistance which exists between the flat solid surface of the metal cylinders and the sample material.

In exemplary embodiments described above, DC resistance measurements can be used. However, AC resistance measurements can also be used.

In an exemplary test using the foregoing embodiment, a sample of cathode paste was worked into the channel region and the recessed portions. Resistance and impedance of the cathode paste placed into the recessed portions of the cylindrical well regions and the channel region were then measured across the two metal cylinders included in the ½" diameter cylindrical well regions. Using a DC resistance measurement, a resistance value of 80±10 kohm was obtained, corresponding to a resistivity of 800±100 ohm cm. Another measurement on the same sample 48 hours later gave a resistance of 90±6 kohm, corresponding to a resistivity of 900±60 ohm cm.

In an alternate test, the resistance was measured with an AC impedance technique. The impedance at frequencies ranging from 50000 Hz to 500 Hz was measured using a Schlumgerger-Solartron model 1250 frequency response analyzer. The data was analyzed by considering an equivalent circuit which consisted of a resistor and a capacitor in parallel. The result of the analysis gave a resistance value of 85 kohm, corresponding to a resistivity of 850 ohm cm.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. Apparatus for measuring electrical characteristics of a material comprising:

means for receiving a sample of material, said receiving means having a first charge conducting region with a first cross-sectional area and a second charge conducting region with a second cross-sectional area, said first cross-sectional area being greater than said second cross-sectional area, said first charge conducting region having at least two well regions formed in a non-conductive material and said second charge conducting region having a channel region formed in said non-conductive material for interconnecting said two wells regions; and means for receiving and conducting an electric charge through said first and second charge conducting regions, said conducting means further including a conductive cylinder located in each of said well regions, each of said conductive cylinders having a first flat conductive surface for contacting said material in said first charge conducting region.

2. Apparatus according to claim 1, wherein said material receiving means is formed with a material resistant to organic solvents.

3. Apparatus according to claim 1, wherein each of said conductive cylinders further includes:

a second end with a recess for receiving a current supply contact.

4. Apparatus according to claim 1, wherein each of said well regions is formed as a cylindrical hole through said non-conductive material.

5. Apparatus according to claim 1, wherein said two well regions are cylindrically shaped through a first length of said non-conductive material, said conducting means further including:

conductive cylinders formed with a first flat surface and formed with a second length less than said first length, one of said conductive cylinders being located in each of said well regions such that an exposed interior of each well region and each of said first flat surfaces forms a recessed portion for receiving said material to be measured.

6. Apparatus according to claim 5, wherein said conducting means includes:

conductive cylinders located in each of said well regions for performing a two probe measurement of conductivity.

7. Apparatus according to claim 6, wherein said material receiving means further includes:

at least one conductive sheet integrally formed in said non-conductive material for providing a separate measurement of said material being measured.

8. Apparatus according to claim 1, wherein said material receiving means further includes:

two conductive sheets integrally formed in said non-conductive material, at least a portion of each of said conductive sheets being exposed in said channel region for measuring a voltage across a portion of said channel region.

9. Apparatus according to claim 1, wherein said material receiving means further includes:

at least one conductive sheet integrally formed in said non-conductive material for providing a separate measurement of said material being measured.

10. Method for measuring electric characteristics of a material, said method comprising the steps of:

placing a first portion of a sample of the material into a recessed portion of a measurement region having a first cross-sectional area, said recessed portion being formed by placing a conductive cylinder into a cylindrically shaped well region;

placing a second portion of the sample of the material into a channel region of the measurement region having a second cross-sectional area less than said first cross-sectional area, said second cross-sectional area being connected with said first cross-sectional area; and conducting an electric charge through said first and second portions of the sample located within said recessed portion and said channel region.

11. Method according to claim 10, wherein said material is conductive paste.

12. Method according to claim 10, wherein said conducting step provides a current measurement through an entire length of said channel region, said method further including the step of:

performing a voltage measurement across a portion of said channel region.

13. Apparatus according to claim 1, wherein each of said two well regions of said first charge conducting region, and said channel region of said second charge conducting region constitute recessed portions in said non-conductive material for receiving said sample of material to be tested.

\* \* \* \* \*